United States Patent
Jo et al.

(10) Patent No.: US 8,932,229 B2
(45) Date of Patent: Jan. 13, 2015

(54) APPARATUS AND METHOD FOR REAL-TIME EMOTION RECOGNITION USING HEART RATE VARIABILITY

(71) Applicant: Electronics and Telecommunications Research Institute, Daejeon (KR)

(72) Inventors: Jun Jo, Daejeon-si (KR); Hyun-Soon Shin, Daejeon-si (KR); Yong-Kwi Lee, Daejeon-si (KR)

(73) Assignee: Electronics and Telecommunications Research Institute, Daejeon-si (KR)

( * ) Notice: Subject to any disclaimer, the term of this patent is extended or adjusted under 35 U.S.C. 154(b) by 0 days.

(21) Appl. No.: 14/017,985

(22) Filed: Sep. 4, 2013

(65) Prior Publication Data

US 2014/0163891 A1 Jun. 12, 2014

(30) Foreign Application Priority Data

Dec. 6, 2012 (KR) .................. 10-2012-0141373

(51) Int. Cl.
*A61B 5/02* (2006.01)
*G06K 9/00* (2006.01)

(52) U.S. Cl.
CPC .................................. *G06K 9/00496* (2013.01)
USPC ........................................................ 600/508

(58) Field of Classification Search
USPC .......................................................... 600/508
See application file for complete search history.

(56) References Cited

U.S. PATENT DOCUMENTS

| | | | |
|---|---|---|---|
| 5,191,524 A * | 3/1993 | Pincus et al. ................... | 600/508 |
| 2008/0221401 A1 * | 9/2008 | Derchak et al. ............... | 600/301 |
| 2009/0292180 A1 * | 11/2009 | Mirow ........................... | 600/301 |
| 2012/0071785 A1 * | 3/2012 | Forbes ........................... | 600/558 |

FOREIGN PATENT DOCUMENTS

| | | |
|---|---|---|
| KR | 10-0397188 | 9/2003 |
| KR | 10-0464821 | 1/2005 |
| KR | 10-0493714 | 6/2005 |
| KR | 10-1115524 | 2/2012 |

* cited by examiner

*Primary Examiner* — Robert N Wieland
(74) *Attorney, Agent, or Firm* — NSIP Law

(57) ABSTRACT

An apparatus and method for recognizing an emotion by use of a heart rate data is provided. The apparatus includes an input signal generation unit configured to receive a plurality of heart rate data, and generate input signals each having a sequence, a signal classification unit configured to classify the input signals into groups, and an emotion recognition unit configured to search for a group, to which the input signal generated by the input signal generation unit belongs, among the groups classified by the signal classification unit, and recognize a user emotion corresponding to the found group.

16 Claims, 6 Drawing Sheets

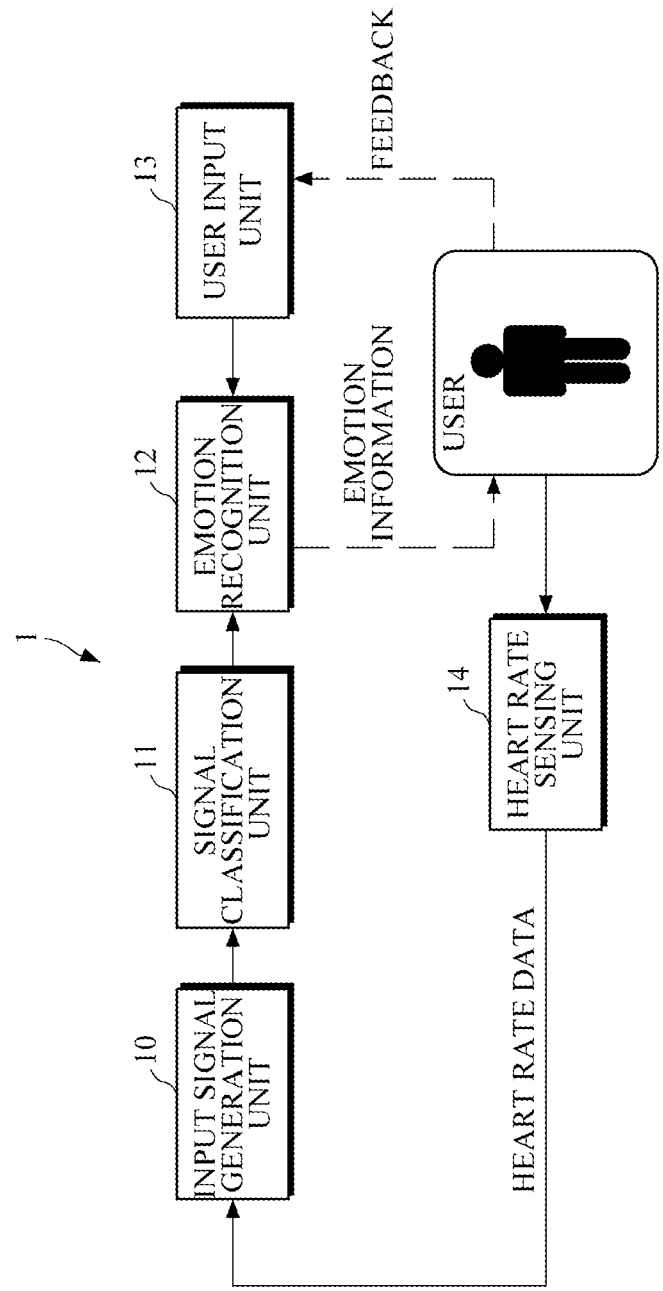

APPARATUS AND METHOD FOR REAL-TIME EMOTION RECOGNITION USING HEART RATE VARIABILITY

CROSS-REFERENCE TO RELATED APPLICATION

This application claims priority from Korean Patent Application No. 10-2012-0141373, filed on Dec. 6, 2012, the entire disclosure of which is incorporated herein by reference for all purposes.

BACKGROUND

1. Field

The following description relates to technology for biomedical information recognition, and more particularly, to technology for recognizing an emotional state of a user in real time using a heart rate variability of the user.

2. Description of the Related Art

For many years, there has been a persistent attempt to measure the emotion of a human in a scientific manner, and in particular, various services and products using the emotion of a human have emerged with the increased interest in the emotion. However, many studies need to be conducted on an emotion measurement method that can be available in practice, and in particular, on an emotion recognition technology suitable for a modern society in which a mobile environment is becoming common. A conventional method of recognizing the emotion or feeling of a human is divided into a method using a biomedical signal such as brainwaves or a heart rate variability, and a method using a voice and a facial expression.

The method using a voice is available for use only when an object speaks and the voice is input, and affected by surrounding noise, and thus is researched and utilized for voice command input technology through speech syntax identification rather than for emotion recognition. Since the recognition of facial expression requires the existent of a camera that faces the object, a condition on using the facial expression is limited, and also since the facial expression can be intentionally changed, a precise emotion recognition is difficult.

A method of recognizing emotion using a biomedical signal has not been developed into a specific recognition method, and in particular, the measuring of brainwaves is complicated, and thus has a difficult in putting into use in a mobile environment. With the recent development and release of a portable electrocardiography, a heart rate variability is easily measured in a mobile environment, but the emotion recognition method using a heart rate variability requires further studies.

SUMMARY

The following description relates to an emotion recognition apparatus and method for providing a service of recognizing the human emotion through measuring a heart rate, capable of effectively classifying and using a heart rate variability.

In one general aspect, an apparatus for recognizing an emotion includes an input signal generation unit, a signal classification unit, and an emotion recognition unit. The input signal generation unit may be configured to receive a plurality of heart rate data, and generate input signals each having a sequence. The signal classification unit may be configured to classify the input signals into groups. The emotion recognition unit may be configured to search for a group, to which the input signal generated by the input signal generation unit belongs, among the groups classified by the signal classification unit, and recognize a user emotion corresponding to the found group.

The input signal generation unit may receive a predetermined number of times of heart rate data in succession, and process the predetermined number of times of heart rate data as a single input signal. The input signal generation unit may checks whether a current input heart rate is increased than a previously input heart rate, and represent increase or decrease of a heart rate in an input signal having a binary form sequence.

The signal classification unit may classify the input signals through a time series data classification. The signal classification unit may calculate an approximate entropy value for the input signal to group input signals each having the same approximate entropy value. The signal classification unit may generate a mapping table in which the input signals are classified in groups.

The emotion recognition unit may recognize the emotion by use of a probability and a random number function. In this case, the emotion recognition unit may sets a probability of being matched to an actual emotion of a user at each group classified by the signal classification unit as a parameter value in advance, generate a random value through the random number function, and compare the parameter value of the found group with the random value generated through the random number function, to recognize the emotion of the user according to result of comparison. The emotion recognition unit may correct the parameter value representing the probability of being matched to the actual emotion of the user at each group classified by the signal classification unit, by reflecting a feedback of the user.

The apparatus may further include a user input unit may configured to receive a feedback of a user about an emotion recognized through the emotion recognition unit, and reflect the feedback on emotion recognition of the emotion recognition unit. The apparatus may further include a heart rate sensing unit configured to sense a heart rate of a user, and transmit the sensed heart rate to the input signal generation unit. The emotion recognition apparatus may be located on a mobile terminal.

In another general aspect, a method of recognizing an emotion using an apparatus for recognizing an emotion includes generating input signals each having a sequence from a plurality of heart rate data, searching for a group, to which the generated input signal belongs, in a mapping table having the input signals classified in groups, and recognizing an emotion of a user corresponding to the found group.

As is apparent from the above description, the emotional state of a user is classified by use of the heart rate variability, and thus the emotion of the user can be easily recognized. In addition, various options are provided when the heart rate variability is converted to a sequence, so that the precision in the user state classification can be adjusted, and the amount of computation and the memory use required for emotion recognition can be adjusted depending on the demand.

In addition, a user-specified personalization is possible when a classification of an input signal generated through the heart rate variability is mapped to the type of emotion, and the emotion recognition function implemented as such may be used in other apparatuses or environments, ensuring a device mobility and expandability.

Other features and aspects will be apparent from the following detailed description, the drawings, and the claims.

BRIEF DESCRIPTION OF THE DRAWINGS

FIG. 1 is a block diagram illustrating an emotion recognition apparatus using a heart rate variability in accordance with an example embodiment of the present disclosure.

Figure 2A:
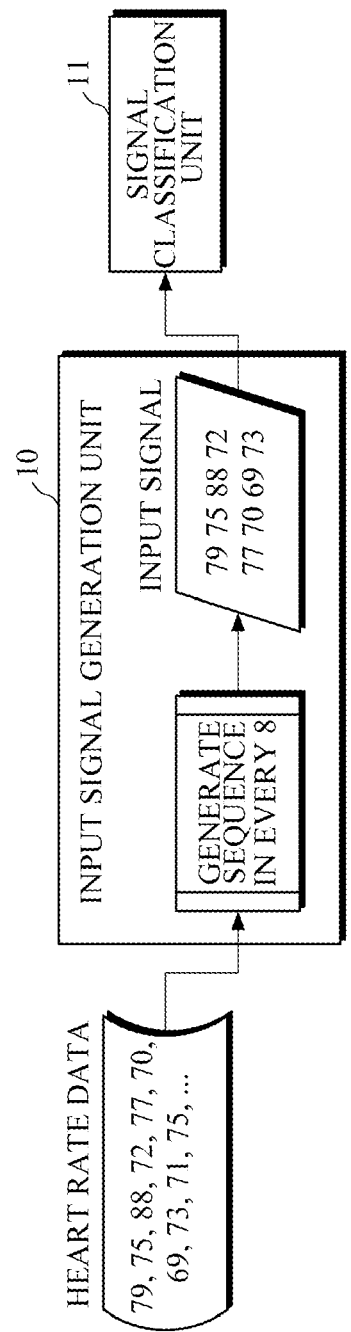
FIGS. 2A and 2B are reference diagrams illustrating examples of generating input signals in an input signal generation unit of FIG. 1 in accordance with various example embodiments of the present disclosure.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness. In addition, terms described below are terms defined in consideration of functions in the present invention and may be changed according to the intention of a user or an operator or conventional practice. Therefore, the definitions must be based on content throughout this disclosure.

FIG. 1 is a block diagram illustrating an emotion recognition apparatus using a heart rate variability in accordance with an example embodiment of the present disclosure.

Referring to FIG. 1, an emotion recognition apparatus 1 may include an input signal generation unit 10, a signal classification unit 11 and an emotion recognition unit 12, and further include a user input unit 13 and a heart rate sensing unit 14.

The emotion recognition apparatus 1 may be an apparatus configured to receive heart rate data of a user, who is a person being measured, in real time to recognize the emotion of the user from the received heart rate data. In particular, the emotion recognition apparatus 1 may be implemented in the form of a mobile terminal that may be carried by a user, in the form of being embedded in a mobile terminal, or in the form of a program.

The input signal generation unit 10 of the emotion recognition apparatus 1 may receive a plurality of heart rate data, and generate an input signal having a series of sequences from the plurality of heart rate data. The heart rate data may be received from the heart rate sensing unit 14 that is configured to sense a heart rate from a user.

The input signal generation unit 10 may sequentially receive a predetermined number of the heart rate data, and process the predetermined number of heart rate data as a single input signal. For example, the input signal generation unit 10 may sequentially receive eight heart rate data, and process the received eight heart rate data as a single input signal.

In accordance with an example embodiment of the present disclosure, the input signal generation unit 10 may generate an input signal having a sequence that simply arranges the heart rate data, without performing a particular process on the heart rate data sequentially received. This example embodiment will be described with reference to FIG. 2A later.

In accordance with another example embodiment of the present disclosure, the input signal generation unit 10 may check whether a current input heart rate is increased than a previously input heart rate, and represent an increase or decrease of the heart rate in an input signal having a binary form sequence. This example embodiment will be described with reference to FIG. 2B later.

Since the complexity and the classification performance of the signal classification unit 11 are determined depending on a sequence generation method of the input signal generation unit 10, the input signal generation unit 10 may be need to be designed in consideration of an allowable computation performance and a reserved memory of a system to which the present disclosure is applied. In addition, depending on the length of an input signal, the number of samples of heart rate used for one-time emotion recognition may be changed. Accordingly, since the time for outputting a result of the emotion recognition may be also changed when the length of the input signal is changed, the input signal generation unit 10 may be desirable to be designed to be appropriate for the system.

The signal classification unit 11 may classify input signals in groups. In particular, the signal classification unit 11 may classify input signals such that the input signals, each having a predetermined length of sequences generated from the input signal generation unit 10, represent respective meanings. In accordance with an example embodiment of the present disclosure, since a heart rate variability which is a component forming an input signal is one type of time series data, a classification method using an approximate entropy (hereinafter, referred to as ApEn), which is one of a statistical classification method for time series data, may be used. An example embodiment of ApEn will be described with reference to FIG. 3. Meanwhile, the signal classification method using ApEn is described only as an example, and various signal classification methods may be used.

The emotion recognition unit 12 may search for a group, to which the input signal generated by the input signal generation unit 10 belongs, among the groups classified by the signal classification unit 11, and recognize an emotion corresponding to the found group. In addition, the emotion recognition unit 12 may provide a user with the result of the emotion recognition. In detail, the emotion recognition unit 12 may map each of the groups classified by the signal classification unit 11 to one type of emotions that are defined in advance. For example, when the signal classification unit 11 classifies the input signals into seventeen groups and the number of the types of emotions desired to be recognized by the emotion recognition apparatus 1 are limited to two, for example, 'joy' and 'sadness', the emotion recognition unit 12 may determine one of the 'joy' and 'sadness' with respect to each of the classified seventeen signal groups, and map the determined one to each group.

In accordance with another example embodiment of the present disclosure, the emotion recognition unit 12, in order to effectively perform mapping between the input signal and the emotion, may update a mapping table by reflecting a feedback of the user. Such an update may be achieved by interoperation between the emotion recognition unit 12 and the user input unit 13. That is, the emotion recognition unit 12 may notify a user with the result of recognition by providing the recognized emotional state, receive a user feedback, that is, information indicating whether a correct result is provided to the user, from the user, and update the mapping table. The example embodiment thereof will be described with reference to FIG. 4 later.

The user input unit 13 may transmit a user response to the emotion recognition unit 12 in response to the result of recognition provided from the emotion recognition unit 12. For example, a user may transmit an answer of positive if the user emotion recognized by the emotion recognition unit 12 is correct, and an answer of negative if the user emotion recognized by the emotion recognition unit 12 is incorrect. Further, the user input unit 13 may provide the answer of positive or negative in a numeric form.

Figure 2B:
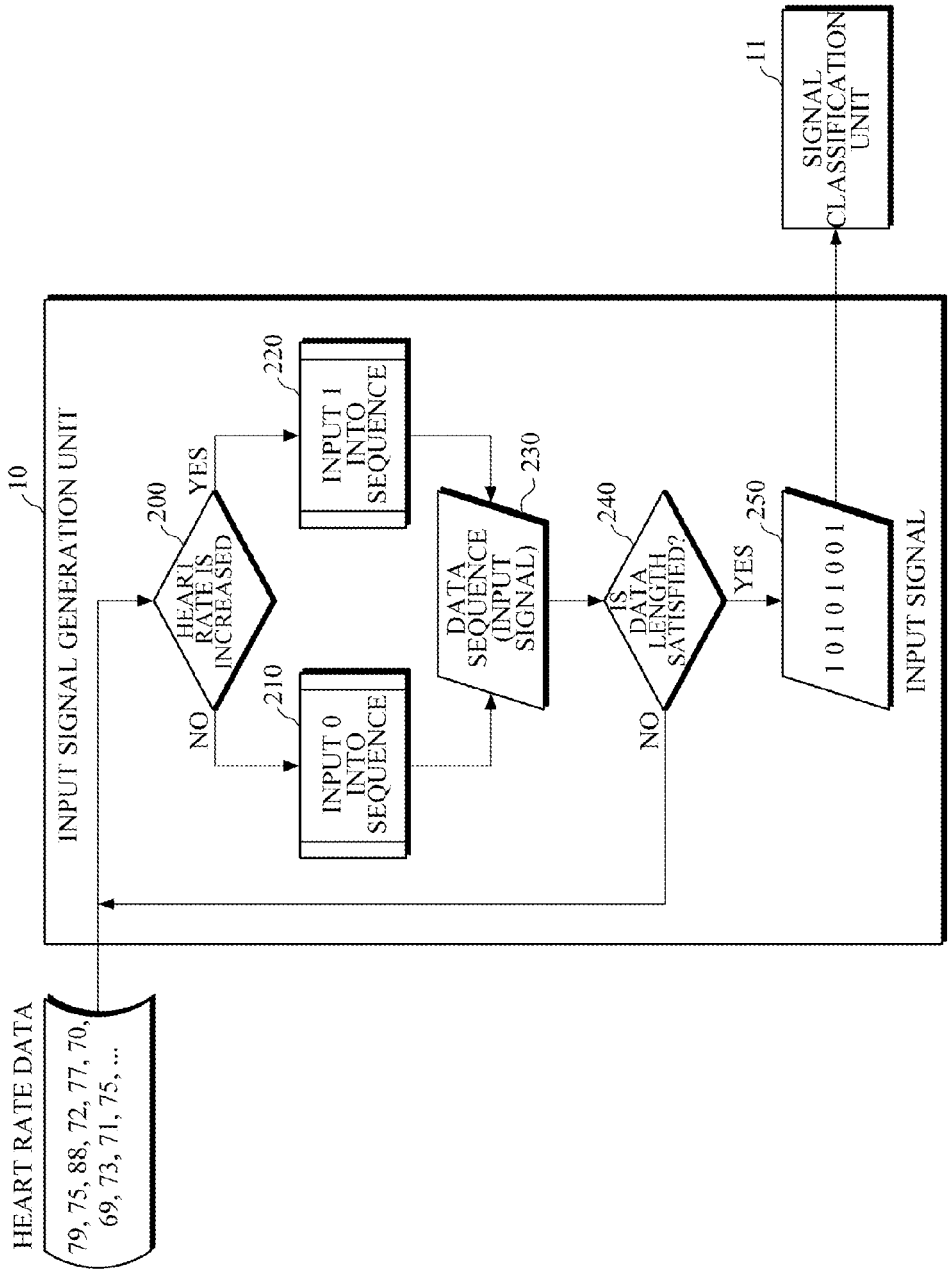

FIGS. 2A and 2B are reference diagrams illustrating examples of generating input signals in an input signal generation unit of FIG. 1 in accordance with various example embodiments of the present disclosure.

Referring to FIG. 2A, when the input signal generation unit 10 in accordance with an embodiment of the present disclosure is assumed to receive heart rate data (79, 75, 88, 72, 77, 70, 69, 73, 71, 75, . . . and so on) in succession, the input signal generation unit 10 may generate an input signal (79, 75, 88, 72, 77, 70, 69 and 73) having a sequence by simply arranging the successive input heart rate data up to a predetermined number of times, for example, up to eight times, without performing a particular processing.

Referring to FIG. 2B, the input signal generation unit 10 may check whether a current input heart rate is increased than a previously input heart rate, and represents an increase and decrease of the heart rate in an input signal having a binary form sequence. For example, as shown in FIG. 2B, when heart rate data (79, 75, 88, 72, 77, 70, 69, 73, 71, 75, . . . and so on) are received in succession, the input signal generation unit 10 may generate a data sequence (230) having a binary form sequence by representing a decrease of the heart rate as 0 (210) and an increase of the heart rate as 1 (220). Thereafter, it is determined whether the data sequence satisfies a predetermined data length, for example, eight (240), and if satisfied, an input signal having the form of {10101001} is finally generated (250).

Figure 3:
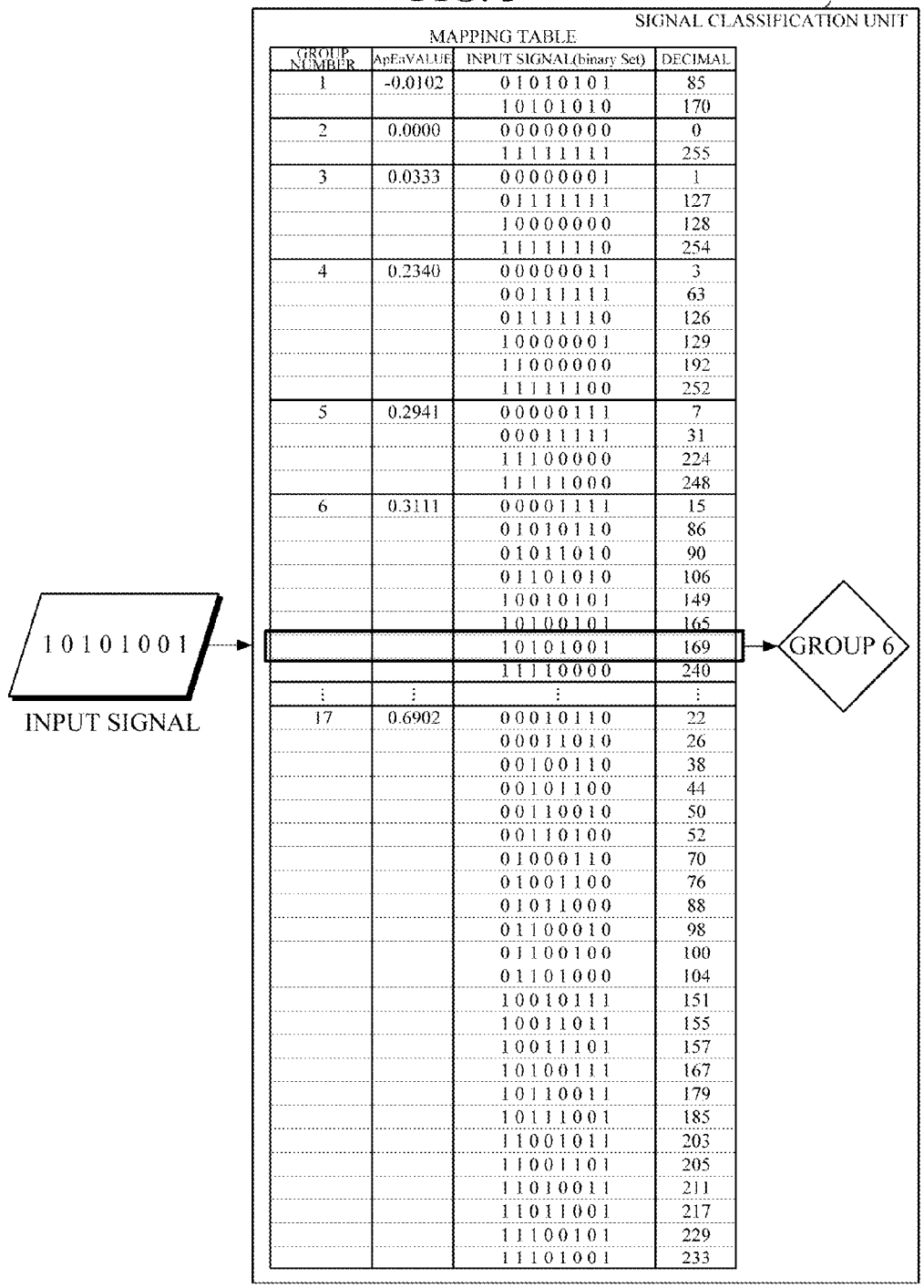
FIG. 3 is a reference diagram illustrating an example of classifying signals by use of approximate entropies in a signal classification unit of FIG. 1 in accordance with an embodiment of the present disclosure.

FIG. 3 is a reference diagram illustrating an example of classifying signals by use of approximate entropies in a signal classification unit of FIG. 1 in accordance with an embodiment of the present disclosure.

Referring to FIG. 3, ApEn, suggested by S. M Pincus in 1991, is a method of quantifying the degree of freedom of change of a given time series data. ApEn may be calculated as the following equation.

STEP 1: the total of N pieces of time series data u(1), u(2), . . . , u(N) are obtained.

STEP 2: the length of data (m: integer) to be compared at one time, and a filtering coefficient (r: real number) are set depending on situations.

STEP 3: m-dimensional vectors x(1), x(2), . . . , x(N−m+1) defined in the form of x(i)=[u(i), u(i+1), . . . , u(i+m−1)] are extracted from the given time series data.

STEP 4: With respect to all cases of i satisfying $1 \leq i \leq N-m+1$, $$C_i^m(r) = \frac{(\text{number of } x(j) \text{ such that } d[x(i), x(j)] < r)}{N - m + 1}$$

is obtained. At this time, $$d[x(i), x(j)] = \max_{k=1,\ldots,m} |u(i+k-1) - u(i+k-1)|$$

is defined.

STEP 5: The ApEn value of the time series data u(1), u(2), . . . , u(N) is calculated as $$A_p E_n = \log(\Phi^m(r)) - \log(\Phi^{m+1}(r)) = \frac{\sum_{i=1}^{N-m+1} C_i^m(r)}{N - m + 1}$$

According to the definition of ApEn, if the calculated ApEn for each input signal is same even if the forms of the input signals are different from each other, since the degree of freedom of change of heart rate may be the same, that is, the change pattern may be considered as the same, the signal classification unit 11 may classify the signals having the same ApEn into the same state. For example, when the input signal is composed of 0 and 1, and is defined as a sequence having a length of 8, the number of cases of the input signal may be $2^8=256$, and when ApEn is calculated for each input signal and the input signals having the same ApEn are classified into one group, a total of 17 groups may be provided in a case of m=1 and r=1. That is, 256 of input patterns may be simplified into 17 groups. The detailed result thereof is illustrated in FIG. 3. When such a classification method is applied to a system in practice, ApEn values may be calculated in advance with respect to all the possible input signals for each form of input signals so as to be applied to a mapping table, thereby providing benefit in configuring a real time processing system.

Figure 4:
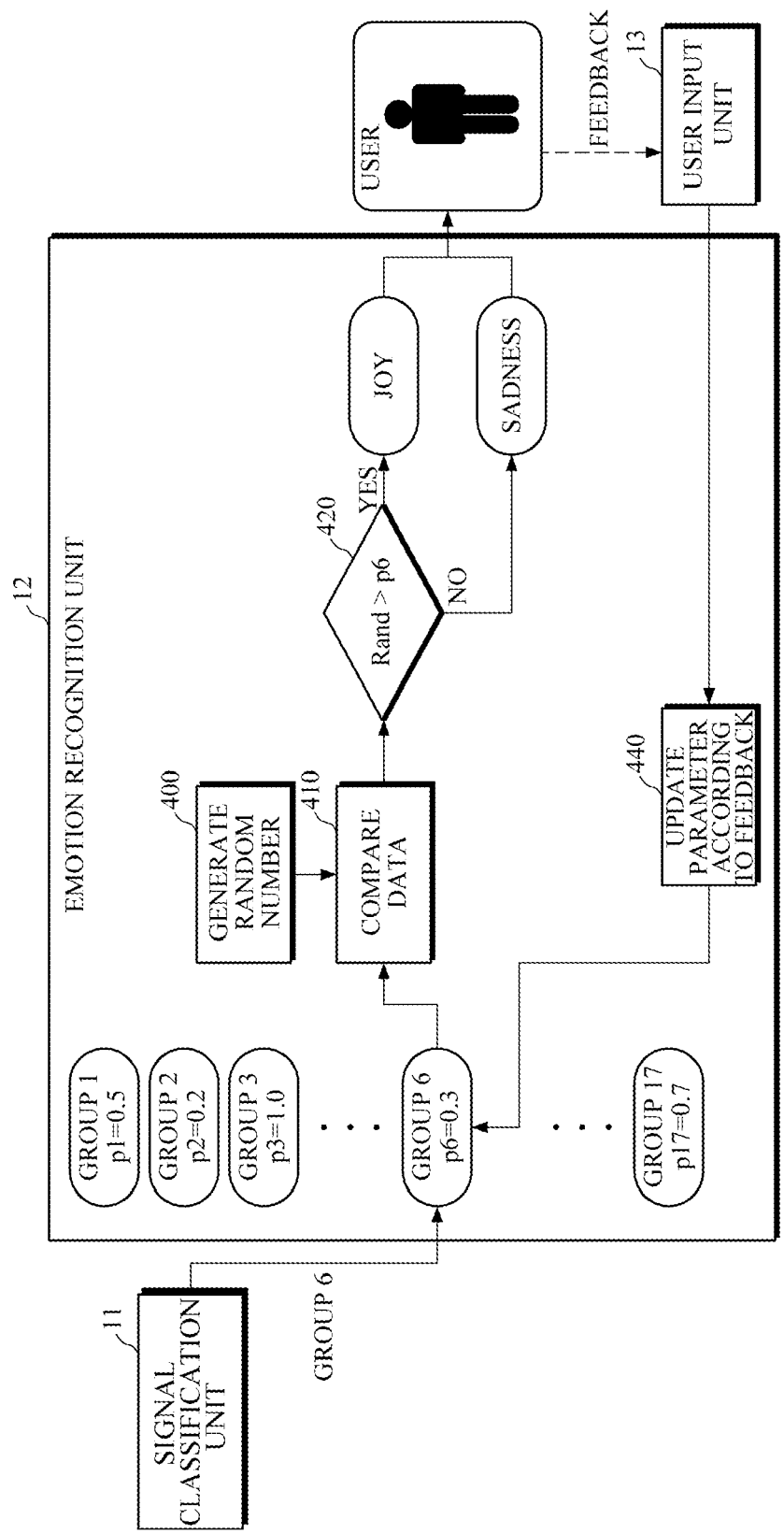
FIG. 4 is a reference diagram illustrating an example of recognizing a user emotion in an emotion recognition unit of FIG. 1 in accordance with an embodiment of the present disclosure.

FIG. 4 is a reference diagram illustrating an example of recognizing a user emotion in an emotion recognition unit of FIG. 1 in accordance with an embodiment of the present disclosure.

Referring to FIG. 4, the emotion recognition unit 12 may set a probability of being matched to the actual user emotion at each of the groups classified by the signal classification unit 11, as a parameter value in advance. For example, as shown in FIG. 4, group 6 has a parameter value of p6=0.3. The parameter value may represent that in a case in which a biomedical signal pattern corresponding to group 6 is input, the probability that the emotion of a user corresponds to 'joy' is 0.7 and the probability that the emotion of the user corresponds to 'sadness' is 0.3

Thereafter, the emotion recognition unit 12 may generate a random value through a random number function Rand ( ) (400). For example, the random number function Rand (0, 1) may be a function to generate a random value ranging between 0 and 1.

Thereafter, the emotion recognition unit 12 may compare the parameter value corresponding to the found group with the random value generated through the random number function Rand (0, 1), and recognize the emotion of a user through the result of comparison. For example, as shown in FIG. 4, in a case in which a value generated from the result of the random number function Rand (0, 1) is 0.5, which results in Rand (0,1)=0.5>0.3=p6, and the emotion state of a user may be recognized as 'joy', and in the contrary, the emotion state of a user may be recognized as 'sadness' (420).

Thereafter, the parameter value determined as p6=0.3 may be updated to a different value according to a user feedback (440). That is, when a recognition result of 'joy' is provided to a user, and a feedback indicating that the result is correct is received from the user, the parameter value p6 may be updated to be decreased by a predetermined reference value, that is, 0.1 into p6=0.2, and as a result, the probability that group 6 is to be recognized as 'joy' may be increased.

Figure 5:
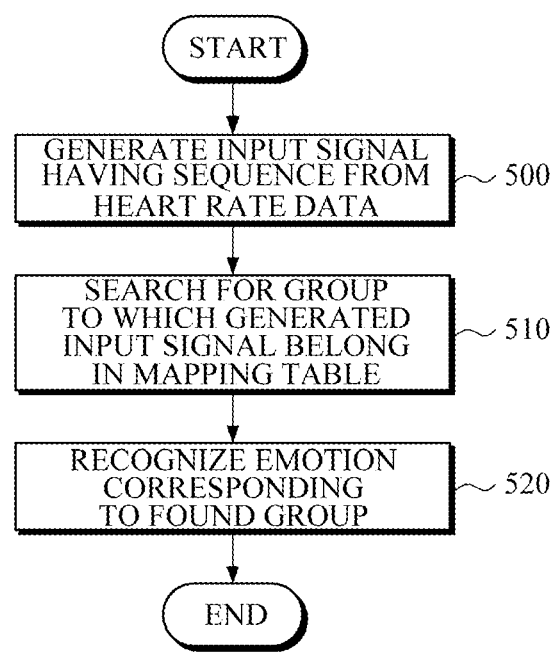
FIG. 5 is a flowchart showing an emotion recognition method using an emotion recognition apparatus in accordance with an embodiment of the present disclosure.

FIG. 5 is a flowchart showing an emotion recognition method using an emotion recognition apparatus in accordance with an embodiment of the present disclosure.

Referring to FIG. 5, the emotion recognition apparatus may generate input signals each having a sequence, from a plurality of heart rate data (500). In accordance with an example embodiment of the present disclosure, in operation 500, the emotion recognition apparatus may receive heart rate data in succession, check whether a current input heart rate is increased than a previously input heart rate, and represent increase and decrease of a heart rate in an input signal having a binary form sequence.

Thereafter, the emotion recognition apparatus may search for a group, to which the generated input signal belongs, in a mapping table having the input signals classified in groups (510). In accordance with an example embodiment of the present disclosure, in operation 510, the mapping table searched by the emotion recognition apparatus may have information generated by calculating ApEn for each input signal and grouping input signals having the same approximate entropy value.

Thereafter, the emotion recognition apparatus may recognize the user emotion corresponding to the found group (520). In accordance with an example embodiment of the present disclosure, in operation 520, the emotion recognition apparatus may set the probability of being matched to an actual emotion of a user at each of the classified groups as a parameter value in advance, generate a random value through a random number function, and compare the parameter value of the found group with the random value generated through the random number function, and then recognize the emotion of the user according to the result of comparison.

Further, the emotion recognition apparatus may receive a feedback of the user about the recognized emotion, and reflect the feedback on emotion recognition.

The present invention can be implemented as computer readable codes in a computer readable record medium. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for recognizing an emotion, the apparatus comprising:
    an input signal generation unit configured to receive a plurality of heart rate data and generate an input signal;
    a signal classification unit configured to classify prospective input signals into groups; and
    an emotion recognition unit configured to find a group to which the input signal generated by the input signal generation unit belongs, among the groups classified by the signal classification unit, and recognize a user emotion corresponding to the found group, wherein
    the input signal generation unit checks whether a current input heart rate differs from a previously input heart rate and represents an increase or a decrease of the current heart rate in the input signal with a binary form sequence.

2. The apparatus of claim 1, wherein the input signal generation unit receives multiple items of heart rate data in succession and processes the multiple items of heart rate data as a single input signal.

3. The apparatus of claim 1, wherein the signal classification unit classifies the prospective input signals through a time series data classification.

4. The apparatus of claim 3, wherein the signal classification unit calculates an approximate entropy value for each prospective input signal so as to group prospective input signals having the same approximate entropy value.

5. The apparatus of claim 1, wherein the signal classification unit generates a mapping table in which the prospective input signals are classified in groups.

6. The apparatus of claim 1, wherein the emotion recognition unit recognizes the emotion by use of probability and a random number function.

7. The apparatus of claim 6, wherein the emotion recognition unit:
    sets a probability of being matched to an actual emotion of a user associated with each group classified by the signal classification unit as a parameter value in advance,
    generates a random value through the random number function, and
    compares the parameter value of the found group with the random value generated through the random number function, so as to recognize the emotion of the user according to the result of comparison.

8. The apparatus of claim 7, wherein the emotion recognition unit corrects the parameter value representing the probability of being matched to the actual emotion of the user associated with each group classified by the signal classification unit, by reflecting feedback of the user.

9. The apparatus of claim 1, further comprising a user input unit configured to receive feedback of a user about an emotion recognized through the emotion recognition unit and reflect the feedback on emotion recognition of the emotion recognition unit.

10. The apparatus of claim 1, further comprising a heart rate sensing unit configured to sense a heart rate of a user and transmit the sensed heart rate to the input signal generation unit.

11. The apparatus of claim 1, wherein the emotion recognition apparatus is located on a mobile terminal.

12. A method of recognizing an emotion that is executed by an apparatus for recognizing an emotion, the method comprising:

generating an input signal from a plurality of heart rate data;

finding a group, to which the generated input signal belongs, in a mapping table having prospective input signals classified in groups; and recognizing an emotion of a user corresponding to the found group, wherein the generating of the input signal comprises:
  receiving the heart rate data in succession,
  checking whether a current input heart rate differs from a previously input heart rate, and
  representing an increase or a decrease of the current heart rate in the input signal with a binary form sequence.

13. The method of claim 12, wherein:
the mapping table comprises information obtained by calculating approximate entropy values for the prospective input signals, and
the groups of prospective input signals each having the same approximate entropy value.

14. The method of claim 12, wherein the recognizing of the emotion of the user comprises:
  setting a probability of being matched to an actual emotion of a user for each of the classified groups as a parameter value in advance;
  generating a random value through a random number function; and
  comparing the parameter value of the found group with the random value generated through the random number function, so as to recognize the emotion of the user according to the result of comparison.

15. The method of claim 14, wherein the recognizing of the emotion of the user further comprises correcting the parameter value representing the probability of being matched to the actual emotion of the user for each of the classified groups, by reflecting feedback of the user.

16. The method of claim 12, further comprising receiving feedback of the user about the recognized emotion and reflecting the feedback for the recognizing of the emotion.

* * * * *